United States Patent
Han et al.

(10) Patent No.: US 7,148,013 B2
(45) Date of Patent: Dec. 12, 2006

(54) COMPLEX OF HEPATITIS B VIRUS POLYMERASE WITH P11 AND METHOD FOR CONTROLLING MOVEMENT OF THE COMPLEX IN HEPG2 CELL

(75) Inventors: Ye Sun Han, Seoul (KR); Juhyun Choi, Bucheon-si (KR); Dae-sik Lim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 322 days.

(21) Appl. No.: 10/637,602

(22) Filed: Aug. 7, 2003

(65) Prior Publication Data

US 2004/0043036 A1   Mar. 4, 2004

(30) Foreign Application Priority Data

Aug. 30, 2002   (KR) .................... 10-2002-0051729

(51) Int. Cl.
*C12Q 1/68*   (2006.01)

(52) U.S. Cl. ............................ 435/6; 435/5

(58) Field of Classification Search ............ 435/6, 435/5
See application file for complete search history.

(56) References Cited

U.S. PATENT DOCUMENTS

2002/0045191 A1 * 4/2002 Schneider et al. ........... 435/7.1

OTHER PUBLICATIONS

Bouchard, M.J. "Activation of Inhibition Cellular Calcium and Tyrosine Kinase Signaling Pathways Identify Targets of the HBx Protein Involved in Hepatitis B Virus Replication" J. Virol. (Jul. 2003) 77, 14, 7713-7719.*
Science vol. 294, Dec. 14, 2001, pp. 2376-2378 "*Calcium Signaling by HBx Protein in Hepatitis B Virus DNA Replication*" by Michael J. Bouchard, Li-Hua Wang and Robert J. Schneider.
The EMBO Journal vol. 16 No. 1 pp. 59-68, 1997 "*Hepadnavirus assembly and reverse transcription require a multi-component chaperone complex which is incorporated into nucleocapsids*" by Jianming Hu, David O. Toft and Christoph Seeger.

* cited by examiner

*Primary Examiner*—Ali R. Salimi
(74) *Attorney, Agent, or Firm*—Jones Day (57) ABSTRACT

Disclosed is a complex of the 11 kDa $Ca^{2+}$ binding protein of 11 and Hepatitis B virus polymerase (HBVPol) which moves to Promyelocytic Leukemia Nuclear Body (PMLNB). Furthermore, the present invention discloses a method for controlling movement of the HBVPol/p11 complex into the nucleus of HepG2 cell with adjusting of intracellular $Ca^{2+}$ ion concentration by administrating an agent for controlling calcium ion concentration in HepG2 cells.

1 Claim, 6 Drawing Sheets

COMPLEX OF HEPATITIS B VIRUS POLYMERASE WITH P11 AND METHOD FOR CONTROLLING MOVEMENT OF THE COMPLEX IN HEPG2 CELL

FIELD OF THE INVENTION

The present invention relates to a complex of the 11 kDa $Ca^{2+}$ binding protein and Hepatitis B virus polymerase (HBVPol) which is involved in Hepatitis B.

BACKGROUND OF THE INVENTION

A connection with liver cancer with infection by Hepatitis B virus (HBV) and use of interferone or a nucleoside analogue for treating the HBV infection, have been reported. However, such treatment has been applicable only for some of the infected patients and could not remove HBV completely. Therefore, there is a need for substrate materials to enhance the curative efficiency against HBV infection.

Studies for finding intracellular factors which bind to HBVPol have been well advanced, and Pol of duck hepatitis B virus, which binds to Hsp90, p23 and Hsp70, shows a possible important role in the virus growth (Hu, J. et al., Hepadnavirus assembly and reverse transcription require a multi-component chaperone complex which is incorporated into nucleocapsids, EMBO J., 16 (1997) 59–68). Although this research was not carried out on HBV capable of infecting humans, HBVPol with multiple enzymatic activities as a single protein, has high possibility of binding intracellular factors and is believed to complete the multiple enzymatic activities through such processing.

HBVPol is expressed in a very low level in *E. coli* or yeast so that biochemical and structural research therefor are not feasible. For this reason, the live viruses have been used or experiments through in vitro eukaryotic expression have been performed. However, these experiments pose a danger according to how they are conducted and the consequent performance thereof involves high costs required to carry them out safely.

SUMMARY OF THE INVENTION

The object of this invention is to provide a carcinogenic mechanism for HBV and provide information for treating cancer by cloning a protein capable of binding to Hepatitis B virus polymerase (HBVPol) and identifying the location of both HBVPol and the protein in human liver to understand the correlation with cell organelles in which they are present.

Specifically, the present invention provides a complex of the 11 kDa $Ca^{2+}$ binding protein and HBVPol, which is involved in Hepatitis B. The structure and amino acid sequence for the 11 kDa $Ca^{2+}$ binding protein is published in Nat Struct Biol. 1999 January; 6(1):89–95 and the amino acid sequence for the Hepatitis B virus polymerase is published in Toh, H., Hayashida, H. and Miyata, T. 1983. Sequency Homology Between Retroviral Reverse Transcriptase and Putative Polymerases of Hepatitis B Virus and Cauliflower Mosaic Virus. Nature; 305: 827–829.

A further object of the invention is to provide a method for controlling movement of the complex in the HepG2 cell.

The invention comprises a complex of the 11 kDa $Ca^{2+}$ binding protein p11 and Hepatitis B virus polymerase, referred to herein as the HBVPol/p11 complex. This complex is characterized as moving to the Promyelocytic Leukemia Nuclear Body (PMLNB). The invention also comprises a method for controlling movement of the HBVPol/p11 complex into the nucleus of a HepG2 cell through adjustment of intracellular concentration of $Ca^{2+}$ ion by administrating an agent which controls the calcium ion concentration in the HepG2 cell. Agents which control calcium ion concentration can increase or decrease the intracellular concentration of $Ca^{2+}$ ion.

DETAILED DESCRIPTION OF THE PREFERRED EMBODIMENTS

The present disclosure is based on investigation of proteins in a human liver cell which bind to Hepatitis B virus polymerase (HBVPol) which is involved in Hepatitis B. It was found that $Ca^{2+}$ binding protein of 11 kDa forms a complex with HBVPol. Also, it was shown that the HBVPol/p11 complex moves to Promyelocytic Leukemia Nuclear Body (PMLNB) which is present in the nucleus of the studied cells and this phenomenon is performed by p11 under influence of intracellular calcium.

Thus, the present invention provides a complex of $Ca^{2+}$ binding protein with HBVPol, wherein p11 binds to HBVPol in a non-covalent manner.

The invention also encompasses a method for controlling movement of the complex into the nucleus of a cell depending on the intracellular concentration of $Ca^{2+}$ ion by administrating a controlling agent for adjusting the calcium ion concentration in a HepG2 cell. The controlling agent can increase or decrease the intracellular concentration of $Ca^{2+}$ ion.

A yeast two-hybrid system was used to search for a protein capable of binding to HBVPol and to identify the location of both HBVPol and the protein in a human liver cell. A variety of yeast strains, such as *Saccharomyces cerevisiae* strain AH109 and Y187 can be used in the yeast two-hybrid system, and all molecular biological manipulation experiments with plasmids were carried out using *E. coli* strain DH5. These are provided by way of example and are not intended to limit the scope of microorganism strains which may be used.

The yeast two-hybrid system comprised a diploid of a yeast library cell which was transformed with the genetic information of a human liver cell and a cell which had the HBVPol related gene. Yeast mating was carried out to screen for factors in the library cell which bind to each HBVPol related proteins. The human $Ca^{2+}$ binding protein (p11) of 11 kDa length was found to bind to HBVPol, and formed a complex with HBVPol in the yeast two-hybrid system.

The p11 that was identified as binding to HBVPol was cloned in a mammalian cell expression vector for application to a human liver cell and then used to transform a human liver cell strain. The transformed human liver cell was reacted with an antibody against p11 and then examined by a confocal laser scanning microscope, with which the location of HBVPol and p11 in the liver cell was identified.

On the basis of the above, the transformed cells were stained with PML antibody and then observed under confocal laser scanning microscope. PMLNB and HBVPol were not in the same location in cells wherein only HBVPol is delivered. HBVPol migrates to PMLNB only in cells wherein p11 is delivered together with HBVPol. This indicates that p11 plays an important role when HBVPol migrates to PMLNB in the human liver cell.

It was also confirmed that when a cell co-delivered with HBVPol and p11 is treated with a calcium channel blocker, HBVPol and p11 migrate to the nucleus of the cell. When cells co-delivered with HBVPol and p11 are treated with a calcium ion concentration increasing agent, HBVPol and p11 remain in the cytoplasm of the cell. Therefore, movement of the HBVPol/p11 complex in the cytoplasm to PMLNB in the nucleus can be controlled by modulating calcium ion concentration in a cell.

The present invention will now be described in detail with reference to the following examples, which are not intended to limit the scope of the invention.

EXAMPLES

<Yeast and Bacteria Used in the Yeast Two-hybrid System of the Invention>

Yeast used in the yeast two-hybrid system of the invention are as shown below and all molecular biological manipulation experiments of plasmids were performed by using *E. coli* strain DH5.

Yeast strain:

*Saccharomyces cerevisiae* AH109 (MATa, trp1-901, leu2-3, 112, ura3-52, his3-200, gal4, gal80, LYS2::GAL1UAS-GAL1TATA-HIS3, GAL2UAS-GAL2TATA-ADE 2URA3::MEL1UAS-MEL1TATA-lacZ, MEL1) (Clontech); and

*Saccharomyces cerevisiae* Y187 (MAT, ura3-52, his3-200, ade2-101, trp1-901, leu2-3, 112, gal4, gal80, met-, URA3::GAL1UAS-GAL1TATA lacZ, MEL1) (Clontech).

<Human Liver Cell Strain and Antibody>

HepG2 (ATCC number: HC-8065) was used as the human liver cell strain. The antibodies used in the Western experiment, immunoprecipitation experiment and immuno fluorescent experiment were anti-Myc mouse and rabbit antibody (Roche), anti-Flag, HA mouse and rabbit antibody (Santa Cruz Biotechnology) and anti-PML mouse antibody (Santa Cruz Biotechnology). To anti-rabbit goat antibody and antimouse goat secondary antibody were attached Rhodamine or FITC (fluorescein isothiocyanate) (Santa Cruz Biotechnology).

Example 1

Yeast Two-hybrid GAL4 System

Yeast (Y187) library (Clontech), which was transformed with the genetic information of a human liver cell, was used to screen factors in the cell, which bind to HBVPol, using MATCHMAKER yeast two-hybrid system (Clontech).

Figure 1:
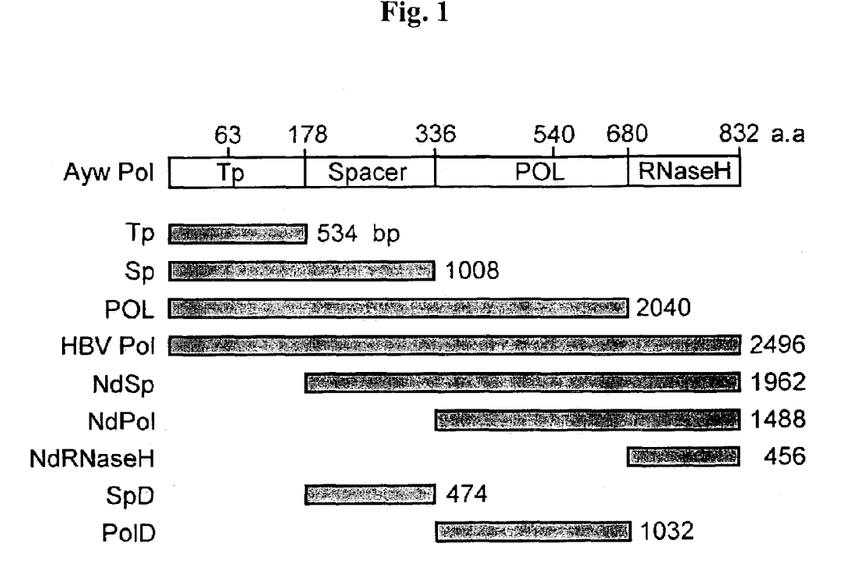
FIG. 1 depicts the HBVPol sequence and deletion variant sequences thereof.

Ayw subtype HBVPol which was designed to have the restriction sites of NdeI at 5' end and SalI at 3' end and 8 domain variants thereof (FIG. 1a) were reacted with 10 units of the restriction enzymes of NdeI and SalI for two hours. Thereafter, the reactants were amplified by PCR consisting of 30 cycles of 95° C. 5 min, 95° C. 30 sec, 54° C. 1 min and 72° C. 3 min and then 1 cycle of 72° C. 7 min. The amplified fragments were reacted with pGBKT7 (Clontech), which was digested with the same restriction enzymes as above, in the presence of T4 DNA ligase of 4 units at 16° C. for 20 hours to clone the amplified fragments in the plasmid.

The AH109 yeast which was intended to be transformed was plated on YPAD plate (1% yeast extract, 2% peptone, 2% dextrose (D-glucose), 0.003% adenine, 2% agar) and grown at 30° C. for 24 hours. Thereafter, 50 µl of yeast was placed into 1.5 ml tube with loop and was washed with 1 ml of sterilized distilled water. The yeast pellet was dissolved in 250 µl of plating solution (40% PEG3350, 0.01 M TE buffer (pH 7.5), 0.1 M lithium acetate (pH 7.5)). To this solution, 5 µl of single stranded DNA (10 mg/ml), 10 µl of 1 M DTT and 1 µg of the above prepared plasmid pGBKT7 were added and stood at a room temperature for 6 hours. Heat shock was given to the cells at 42° C. for 15 minutes and then centrifuged at 3,000 rpm for 1 minute. Thereafter, the supernatant was discarded and the yeast pellet was washed with 1 ml of the sterilized distilled water. 100 µl of TE buffer (pH 7.5) was added to the yeast pellet. The resulting solution was plated on SD-Trp plate and the cells were grown at 30° C.

The above yeast library cells containing the gene library of the human liver cell were grown in a liquid medium including no Leu (containing 0.67% yeast nitrogen base without amino acids, 20 mg/l L-arginine HCl, 30 mg/l L-isoleucine, 30 mg/l lysine HCl, 20 mg/l L-methionine, 50 mg/l L-phenylalanine, 200 mg/l L-threonine, 30 mg/l L-tyrosine, 20 mg/l L-uracil, 150 mg/l L-valine, 20 mg/l adenine, 20 mg/l histidine, 20 mg/l tryptophan and 2% glucose) for 24 hours until $OD_{600}$ reached 0.8.

At the same time, each of the yeast including HBVPol related genes was grown in a liquid medium including no Trp (containing 0.67% yeast nitrogen base without amino acids, 20 mg/l L-arginine HCl, 30 mg/l L-isoleucine, 30 mg/l lysine HCl, 20 mg/l L-methionine, 50 mg/l L-phenylalanine, 200 mg/l L-threonine, 30 mg/l L-tyrosine, 20 mg/l L-uracil, 150 mg/l L-valine, 20 mg/l adenine, 20 mg/l histidine, 100 mg/l leucine and 2% glucose) for 30 hours until $OD_{600}$ reached 0.9. Then, 2 ml of the library cells and each of HBVPol of 50 ml were mixed with 45 ml of YPDA yeast complex media and mated at 30° C. for 20 hours with stirring.

The resulting diploid yeasts were collected and plated on a medium plate including no leu, trp, ade and his (containing 0.67% yeast nitrogen base without amino acids, 20 mg/l L-arginine HCl, 30 mg/l L-isoleucine, 30 mg/l lysine HCl, 20 mg/l L-methionine, 50 mg/l L-phenylalanine, 200 mg/l L-threonine, 30 mg/l L-tyrosine, 20 mg/l L-uracil, 150 mg/l L-valine and 2% glucose) to select the diploid having an interaction between HBVPol and the library proteins.

The genotypes of strain AH109 (MATa, trp1-901, leu2-3, 112, ura3-52, his3-200, gal4, gal80, LYS2::GAL1UAS- GAL1TATA-HIS3, GAL2UAS-GAL2TATA-ADE 2URA3: MEL1UAS-MEL1TATA-lacZ, MEL1) and Y187(MAT, ura3-52, his3-200, ade2-1, trp1-901, leu2-3, 112, gal4, gal80, met-, URA3::GAL1UAS-GAL1TATA LacZ, MEL1), the yeast diploid, wherein the genes incorporated in two yeasts are interacted, were able to grow on solid media including no Ade, His, Trp and Leu. This indicates that HBVPol of AH109 interacts with the library proteins of Y187 (see, Bendixen, C., Gangloff, S., Rothstein, R. (1994) A yeast mating-selection scheme for detection of protein-protein interactions. *Nucleic Acids Res.*, 22, 1778–1779).

Example 2

Co-immunoprecipitation Analysis $Ca^{2+}$ binding protein p11 of 11 kDa, which bind to HBVPol, was screened by using the yeast two-hybrid system and the binding was confirmed by using TNT coupled reticulocyte lysate System (Promega).

Figure 2:
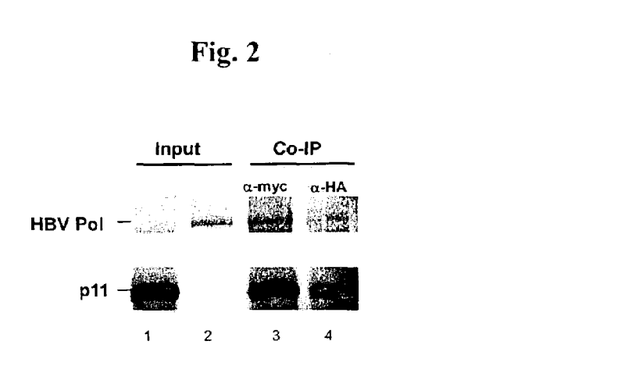
FIG. 2 is a photograph showing in vitro binding assay for HBVPol and p11.

Since open reading frame coding for p11 is cloned to pGADT7 in Y187 yeast cell (Clontech), p11 can be produced by binding L-[35S]-methionine using T7 promoter. was reacted with 1 g of anti-HA mouse antibody at 4° C. for 2 hours. The reactants were precipitated by using protein G plus/protein A agarose bead (Oncogene, Inc.) and analyzed on 15% SDS-PAGE (FIG. 2, lane 1). HBVPol, which was cloned to pGBKT7 as shown in Example 1, was also synthesized and then analyzed in the same way as p11 (FIG. 2, lane 2).

The p11 and HBVPol were stood for 1 hour. Then, HBVPol was reacted with 1 g of anti-Myc at 4° C. for 2 hours and p11 was reacted with 1 g of HA mouse antibody at 4° C. for 2 hours. The reactants were precipitated by using protein G plus/protein A agarose bead (Oncogene, Inc.) and washed to remove any materials which did not bind to HBVPol or p11 having the antibodies bound thereto. Thereafter, the reactants were reacted with SDS loading buffer at 95° C. for 5 minutes and separated from protein G plus/protein A agarose. The separated materials were run on 15% SDS-PAGE to analyze the radioactive products with X-ray film (FIG. 2, lanes 3 and 4).

Lane 3 of FIG. 2 is the result of experiment using anti-Myc mouse antibody for HBV Pol, lane 4 is the result of experiment using HA mouse antibody for p11. The lanes show that the bands of HBV Pol and p11 are present in a separate state, and this means that HBV Pol and p11 form the complex by a non-covalent binding.

Example 3

Preparation of Plasmid for Expression of a Mammalian Cell

The p11 identified in Example 2 was cloned to a plasmid for expression of a mammalian cell for applying the p11 to a human liver cell.

Figure 7:
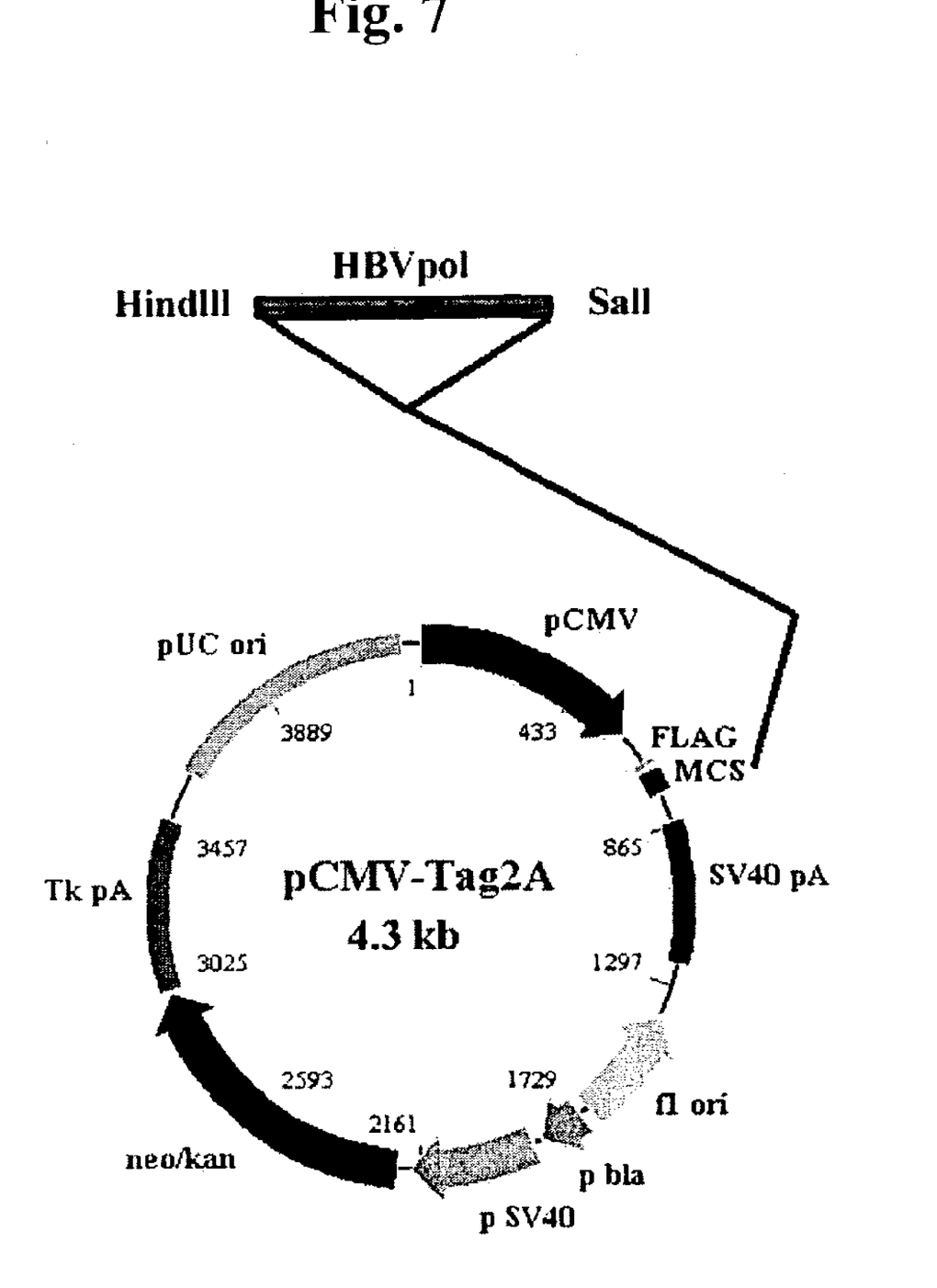
FIG. 7 is a schematic diagram of plasmid pCMV-tag2A comprising a sequence coding for HBVPol.

HBV Pol was amplified by PCR consisting of 1 cycle of 95° C. 5 minutes; 30 cycles of 95° C. 30 seconds, 54° C. 1 minute, 72° C. 3 minutes; and 1 cycle of 72° C. 7 minutes, and then digested with 10 units of HindIII and SalI for 2 hours. The restricted products were ligated to pCMV2A vector (Stratagene), which was restricted with the identical restriction enzymes, with 4 units of ligase per reaction at 16° C. for 20 hours to prepare pCMV-tag2A plasmid containing a HBVPol coding sequence (FIG. 7).

Figure 8:
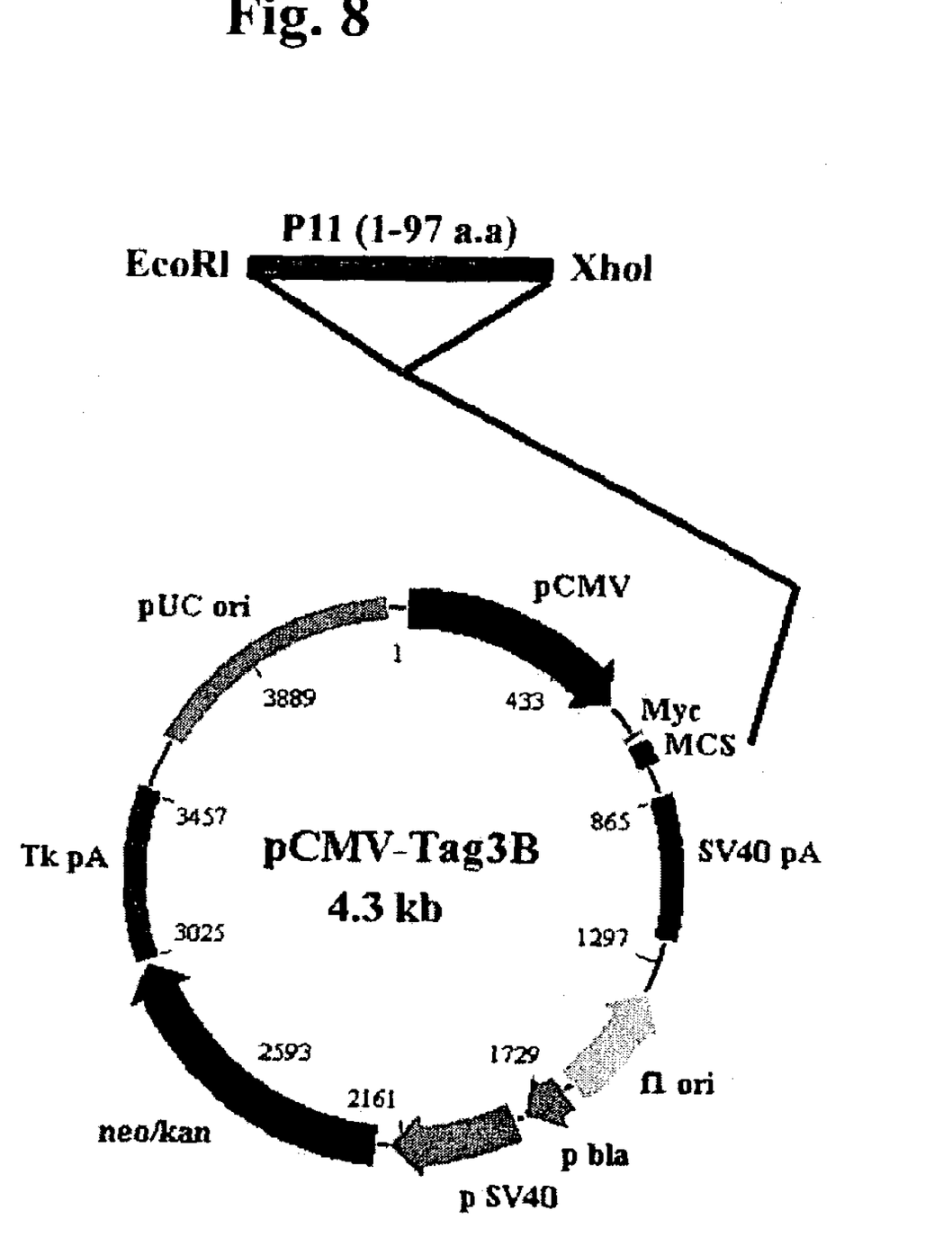
FIG. 8 is a schematic diagram of plasmid pCMV-tag3B comprising a sequence coding for p11.

The p11 was amplified by PCR consisting of 1 cycle of 95° C. 5 minutes; 30 cycles of 95° C. 30 seconds, 55° C. 1 minute and 72° C. 1 minutes; and 1 cycle of 72° C. 7 minutes, and then digested with 10 units of EcoRI and XhoI for 2 hours. The restricted products were ligated to pCMV3B vector (Stratagene), which was restricted with the identical restriction enzymes, with 4 units of ligase per reaction at 16° C. for 20 hours to prepare pCMV-tag3B plasmid containing a p11 coding sequence (FIG. 8).

Example 4

Immunofluorescent Experiment and Microscopy

HepG2 was grown on a chamber slide charged with DMEM (supplemented with 0.1 mM non-essential amino acids and 10% FBS, culturing condition: 37° C., moisturized with a mixture of 95:5% (v/v) air and $CO_2$), and Effectene (Qiagen) was used to deliver genes into the cell. Cells treated with EGTA and to which the gene was delivered, were washed with PBS and fixed with 100% methanol at −20° C. for 15 minutes. The slide was treated with a blocking solution (1% goat serum/PBS) at room temperature for 30 minutes and then reacted with anti-Myc rabbit (1:200) antibody against p11, anti-Flag rabbit (1:200) antibody against HBVPol, or anti-PML mouse (1:200) antibody at 4° C. for one day.

Figure 3:
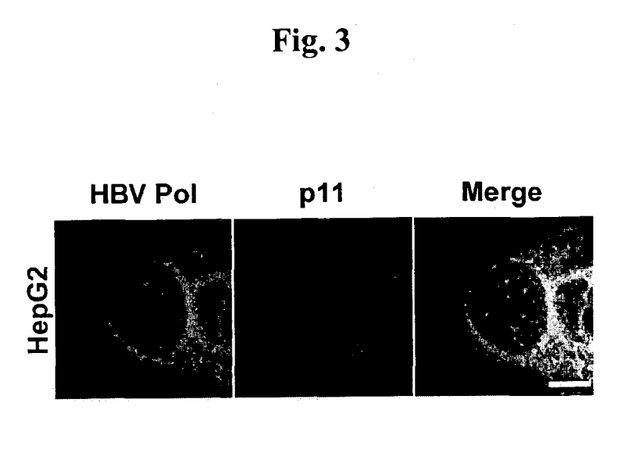
FIG. 3 is a photograph showing location of HBVPol and p11 in HepG2 cells.

After reaction, the cells were reacted with anti-rabbit or anti-mouse goat secondary antibody, to which rhodamine or fluorscein isothiocyanate was attached, at 37° C. and then a coverslip was attached thereto with mounting solution. Thereafter, the stained cells were observed with a confocal laser scanning microscope (CLSM Bio-Rad 1024). FIG. 3 shows photographs of HBVPol, p11 and overlap of two proteins from the left to the right and confirms that the proteins are present with each other while forming dots in a cytoplasm, nucleus membrane and nucleus of HepG2 cell.

Figure 4A:
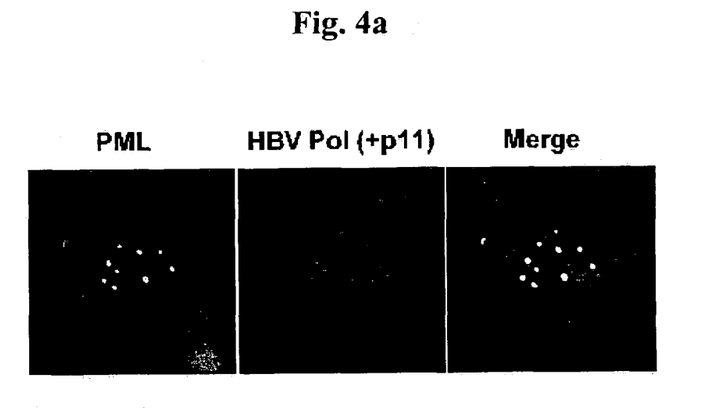
FIGS. 4a to 4c are photographs showing function of p11 to derive HBVPol to Promyelocytic Leukemia Nuclear Body (PMLNB) in HepG2 cells.
Figure 4B:
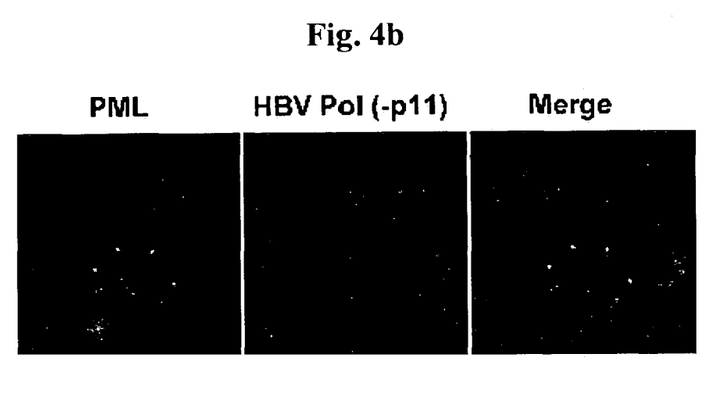
Figure 4C:
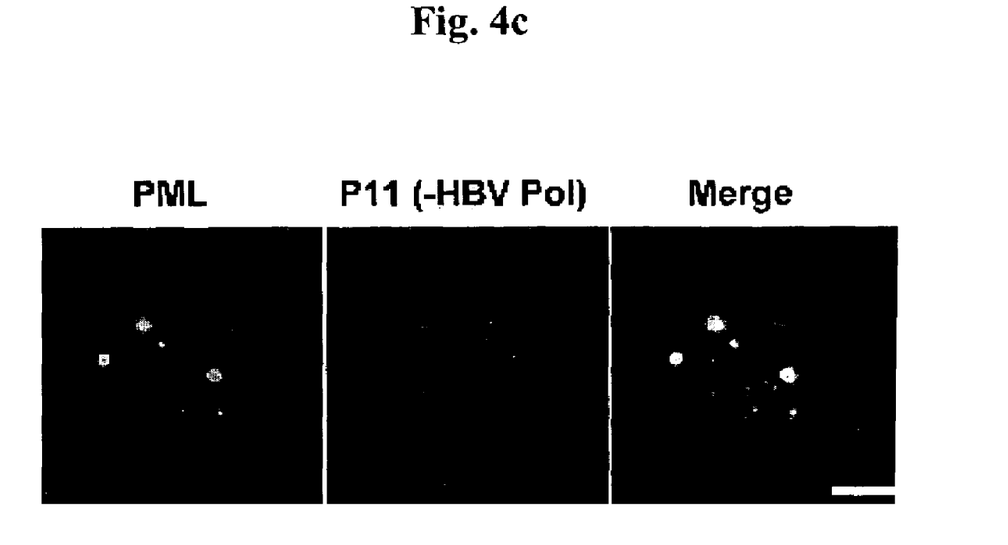

In view of the fact that HBVPol and p11 form dots in the nucleus of the cell, the cell was stained with PML antibody. As a result, it was confirmed that PMLNB was present in the same location with p11 and HBVPol as shown in FIG. 4a. Furthermore, in the cell to which only HBVPol was delivered, PMLNB was not present in the same location with HBVPol (FIG. 4b), while HBVPol moved to PMLNB only in the cell wherein p11 was delivered with HBVPol (FIG. 4c). From these observations, p11 was confirmed to play an important role when HBVPol moves to PMLNB of the human liver cell.

Figure 5A:
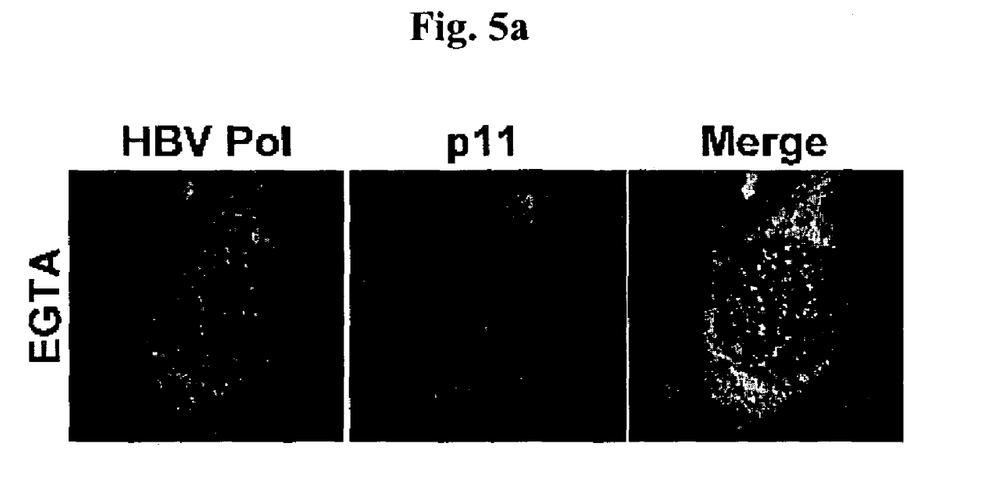
FIGS. 5a and 5b are photographs showing that HBVPol/p11 complex moves in a cell depending on concentration of $Ca^{2+}$.
Figure 5B:
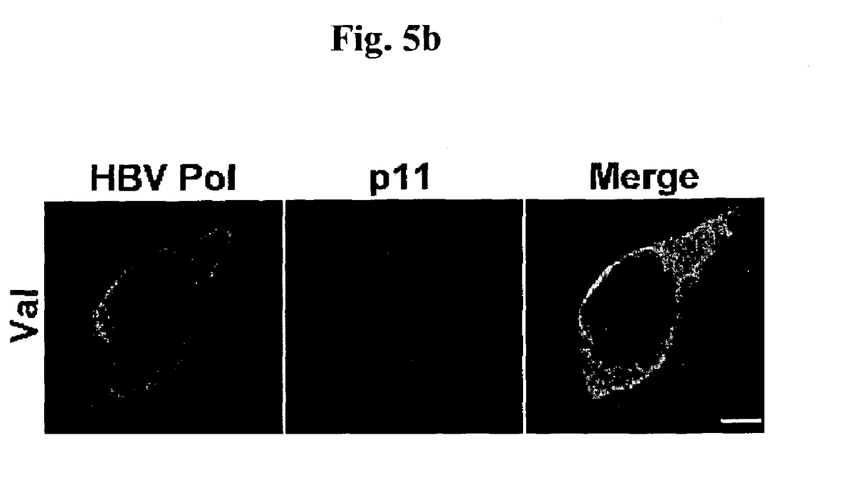

Taking notice that p11 is a $Ca^{2+}$ binding protein, a cell to which HBVPol and p11 are co-delivered was treated with 0.5 mM of a $Ca^{2+}$ ion concentration decreasing agent, EGTA for 48 hours. As a result, it was confirmed that most of HBVPol and p11 migrated into the nucleus of the cell (FIG. 5a), while in cells treated with 30 uM of $Ca^{2+}$ ion concentration increasing agent, valinomycine for 24 hours, HBVPol and p11 remained in the cytoplasm of the cell (FIG. 5b).

As shown in the examples, it was confirmed that HBVPol binds to p11 to form a complex and the complex moves into PMLNB in the nucleus of the cell, at which time, both p11 and a low concentration of $Ca^{2+}$ ion are important factors for movement of HBVPol. Therefore, the intracellular location of p11 and HBVPol can be controlled by adjusting the $Ca^{2+}$ concentration in the cell.

Figure 6:
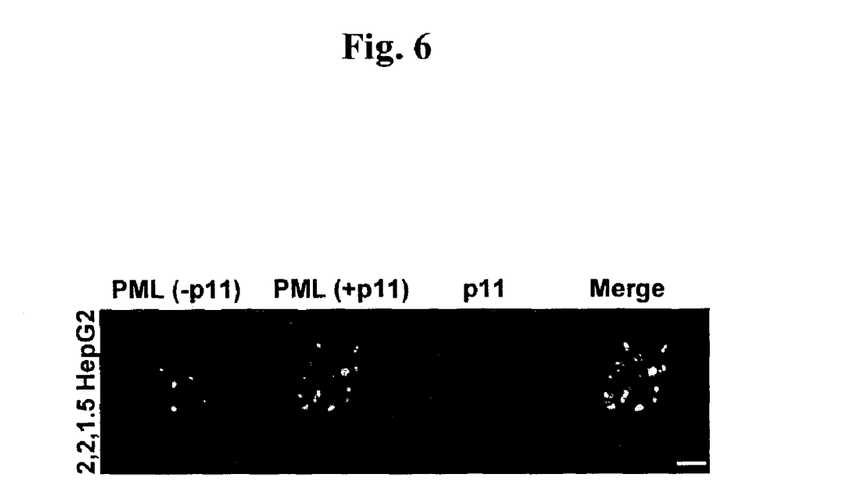
FIG. 6 is a photograph showing that if p11 is present in 2,2,1.5 HepG2 cells in which HBV develops, the size or number of PMLNB is higher than those of PMLNB in a normal cell.

Furthermore, 2,2,1.5 HepG2 was transformed with pCMV-tag3B plasmid to only express p11. The p11 was reacted with anti-Myc rabbit (1:200) antibody against p11 and observed with a confocal laser scanning microscope (CLSM Bio-Rad 1024). When p11 is present in 2,2,1.5 HepG2 cell wherein the HBV develops, the size and number of PMLNB was confirmed to be higher than those of PMLNB in a normal cell (FIG. 6).

Although it was reported that the size and number of PMLNB in hepatocellular carcinoma (HCC) patient by HBV infection increase as the cancer progresses (Yoon, G. S., 2001, J. Korean Med. Sci., 16, 433–438), it is the present invention that ascertains that increase of the size or number of PMLNB is caused by p11.

According to the present invention which confirms that p11 induces movement of HBVPol to PMLNB of a liver cell depending on $Ca^{2+}$ concentration in the cell, various targets for treating liver cancer can be provided.

What is claimed is:

1. A method for remaining a complex of a 11 kDa $Ca^{2+}$ binding protein p11 and a Hepatitis B virus polymerase (HBVPol) in the cytoplasm of a HepG2 cell, said method comprising the steps of:
   a) treating the HepG2 cell with an agent that increases an intracellular calcium ion concentration; and
   b) preventing the complex from migrating to a nucleus of the HepG2 cell.

* * * * *